United States Patent
Shumka et al.

(10) Patent No.: US 10,502,662 B2
(45) Date of Patent: Dec. 10, 2019

(54) EDDY CURRENT ARRAY TECHNOLOGY FOR ASSESSING WHEELS AND RIMS OF OFF ROAD VEHICLES

(71) Applicants: Thomas Shumka, Kelowna (CA); Jason Shumka, Kelowna (CA)

(72) Inventors: Thomas Shumka, Kelowna (CA); Jason Shumka, Kelowna (CA)

(73) Assignee: OTR RIM CERTIFICATON, INC., Kelowna, BC (CA)

(*) Notice: Subject to any disclaimer, the term of this patent is extended or adjusted under 35 U.S.C. 154(b) by 117 days.

(21) Appl. No.: 15/129,373

(22) PCT Filed: Mar. 25, 2015

(86) PCT No.: PCT/IB2015/052209
§ 371 (c)(1),
(2) Date: Sep. 26, 2016

(87) PCT Pub. No.: WO2015/145378
PCT Pub. Date: Oct. 1, 2015

(65) Prior Publication Data
US 2017/0176294 A1    Jun. 22, 2017

Related U.S. Application Data

(60) Provisional application No. 61/970,308, filed on Mar. 25, 2014.

(30) Foreign Application Priority Data

Mar. 25, 2015 (WO) .................. PCT/IB2015/052209

(51) Int. Cl.
*G01N 27/90* (2006.01)
*G01M 17/013* (2006.01)

(52) U.S. Cl.
CPC ........ *G01M 17/013* (2013.01); *G01N 27/902* (2013.01); *G01N 27/9086* (2013.01)

(58) Field of Classification Search
USPC ......................................... 324/229, 240–243
See application file for complete search history.

(56) References Cited

U.S. PATENT DOCUMENTS

| 4,509,295 A | 4/1985 | Bottcher et al. |
| 5,636,026 A | 6/1997 | Mian et al. |

(Continued)

FOREIGN PATENT DOCUMENTS

| CA | 1198203 | 12/1985 | | |
| WO | WO 9116985 A1 * | 11/1991 | ............... | B03C 1/23 |

OTHER PUBLICATIONS

International Search Report and Written Opinion dated Jul. 16, 2015 in PCT/IB2015/052209 (13 pages).

*Primary Examiner* — Vincent Q Nguyen
(74) *Attorney, Agent, or Firm* — Baumgartner Patent Law; Marc Baumgartner

(57) ABSTRACT

A method of examining a wheel or rim on site is provided using an eddy current array probe in electronic communication with a computer, the computer having a processor and a memory, the memory to provide instructions to the processor. The method involves standardizing the eddy current array probe with a reference standard, adjusting the eddy current array probe with a lift off screw to provide a suitable distance between the probe and a surface of the wheel or rim, scanning the wheel or rim with an alternating current, sending a data set to the computer, the computer analyzing the data set, and the computer displaying a three-dimensional image of the data set on a user interface. This method is particularly developed for off road vehicles at mining sites or any off road vehicle wheels and rims.

9 Claims, 7 Drawing Sheets

(56) References Cited

U.S. PATENT DOCUMENTS

| | | |
|---|---|---|
| 6,952,094 B1 | 10/2005 | Viertl |
| 8,237,433 B2 | 8/2012 | Goldfine |
| 8,264,221 B2 | 9/2012 | Faucher |
| 2004/0004475 A1* | 1/2004 | Goldfine ............... G01N 27/82 324/242 |
| 2009/0001226 A1 | 1/2009 | Haygood |
| 2016/0025682 A1 | 1/2016 | Walker |

* cited by examiner

Box #10 – Probe
Box #12 – Sensor
Box #14 – Distal end
Box # 16 – Proximal end
Box #29 – Instrument
Box #50 – Computer
Box #52 – Processor
Box #54 – Memory
Box #56 – User interface
Element #58 – Three-dimensional image Box #50 – Computer
Element #104 – Shoe
Element #108 – Sensor layer
Element #124 – Sensor
Element #140 – Plurality of coils
Element #142 – Eddy current array
Element #144 – Drive coil
Element 146 – Sensing coil
Element #48 – Multiplexer
Element#150 - Channels
Element #160 – Lift off screw
Element #164 – Gauge
Element #166 – Processor
Element #168 – Circuit board

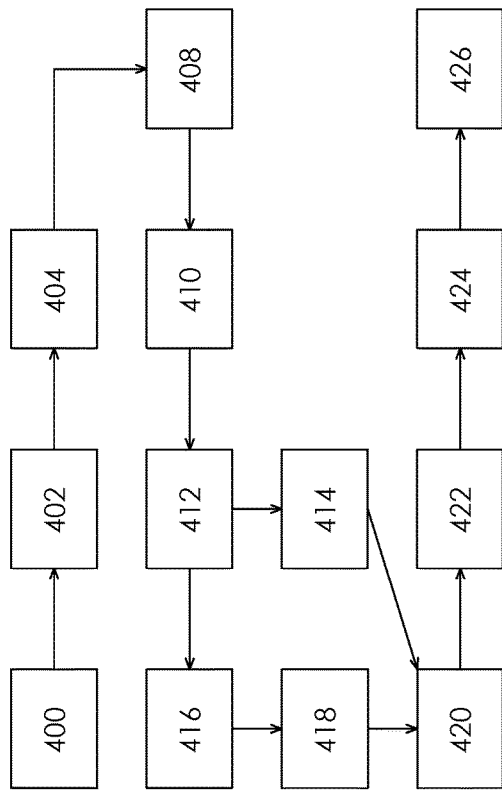

FIG. 6

Box #400 – Surface is cleaned
Box #402 – Probe is standardized
Box #404 – Probe is placed on surface
Box #408 – Lift off is set
Box #410 – Surface is scanned
Box #412 – Speed is controlled
Box #414 – Alternating current produces a uniform magnetic field
Box #416 – Alternating current leads to a non-uniform magnetic field
Box #418 – The signal provides position and depth information
Box #420 – The signal is processed
Box #422 – Memory provides instructions to the processor
Box #424 – Depth, length and position information is provided
Box #426 – A three-dimension image is produced
Box #428 – The image is displayed
Box #430 – The data are archived

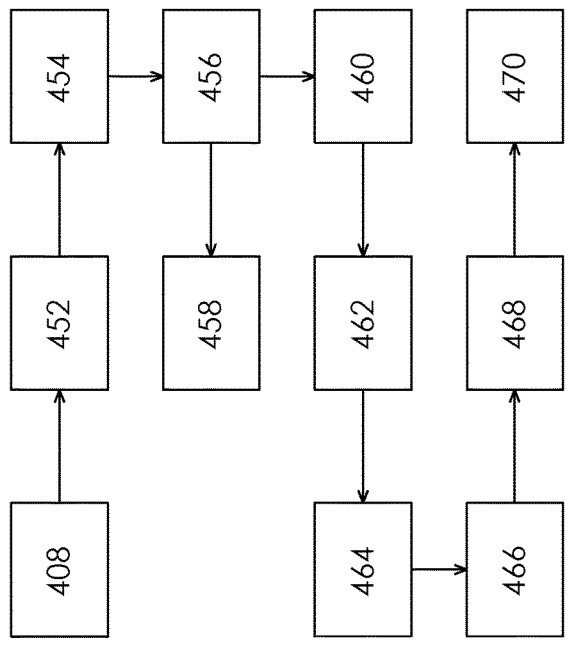

FIG. 7

Box #408 – Lift off is set
Box #452 – Probe fails to send signal
Box #454 – The processor uses instructions from the memory
Box #456 –The signal or lack thereof is processed
Box #458 – A pass reading is produced
Box #460 – A fail reading is produced
Box #462 – The memory provides instructions to the processor
Box #464 – The processor uses the instructions
Box #466 – The provides data on wear
Box #468 – The data are further processed
Box #470 – Predictive models are produced

EDDY CURRENT ARRAY TECHNOLOGY FOR ASSESSING WHEELS AND RIMS OF OFF ROAD VEHICLES

CROSS REFERENCE TO RELATED APPLICATIONS

The present invention is filed under 35 U.S.C. § 371 as the U.S. national phase of International Application No. PCT/IB2015/052209, filed Mar. 25, 2015, which designated the U.S. and claims the benefit of U.S. Provisional Patent Application No. 61/970,308 filed Mar. 25, 2014, each of which is hereby incorporated in its entirety including all tables, figures, and claims.

FIELD

The present technology is a non-destructive method of testing wheels and rims of off-road (OTR) vehicles for defects and wear. More specifically, the method uses eddy current array technology to measure wear and detect defects of rolled steel wheels and rims for off road vehicles, such as mining and oil and gas vehicles on site.

BACKGROUND

Eddy current array technology is a widely used for quality control testing on objects such as wire, rods or tubes. This testing often involves having the test objects travel along a work path, passing through eddy current probe(s).

Eddy current testing (as opposed to eddy current array testing) can be performed on discs and other shaped objects constructed of conductive and/or non-magnetic materials to look for defects and wear. Eddy current testing may use eddy current coils designed to generate a changing magnetic field that may interact with the disc to generate an eddy current. Variations in the phase and magnitude of the generated eddy current may be measured by measuring changes to the current flowing in the coil. Alternatively, changes in phase and magnitude of the generated eddy current may be measured using a second coil. Changes in the phase and magnitude of the generated eddy current may indicate one or more flaws in the discs, such as small cracks that may lead to failures if not addressed. While eddy current inspection methods may provide equivalent sensitivity to magnetic particle inspection methods, current eddy current inspection methods are limited to single small element and rigid array probes. Due to their small size and rigidity, such probes make inspection of large discs and other large components that have varying and multiple geometries difficult and time-consuming, and therefore expensive.

Eddy current sensor arrays have been employed to measure stress on airplane parts, for example, on the landing gear, and to measure weights of components. For example, U.S. Pat. No. 8,237,433 discloses methods for monitoring of stresses and other material properties. These methods use measurements of effective electrical properties, such as magnetic permeability and electrical conductivity, to infer the state of the test material, such as the stress, temperature, or overload condition. The sensors, which can be single element sensors or sensor arrays, can be used to periodically inspect selected locations, mounted to the test material, or scanned over the test material to generate two-dimensional images of the material properties. Magnetic field or eddy current based inductive and giant magnetoresistive sensors may be used on magnetizable and/or conducting materials, while capacitive sensors can be used for dielectric materials. Methods are also described for the use of state-sensitive layers to determine the state of materials of interest. These methods allow the weight of articles, such as aircraft, to be determined. The probes in use would not be suitable for assessing wear and identifying surface defects in wheels and rims in remote locations, nor would they be suitable for use on abrasive surfaces, as could occur on a wheel or rim.

Eddy current arrays can also be used in production and inspection lines. For example, U.S. Pat. No. 8,264,221 discloses an eddy current probe assembly suitable for inspecting a test object with longitudinal shape, being passed through the assembly in the object's axial direction during an inspection session, the probe assembly comprising multiple probe modules being disposed in a radial plane and with the modules partially overlaying on each other forming an IRIS structure encircling an inspection zone, wherein a movement in unison of each of the probe modules closer to or further away from the center of the inspection zone makes the inspection zone enlarged or contracted. Spring tension is applied on each of the probe modules so that constant life-off in maintained between the probe modules and the test surface. Array of eddy current elements for each probe module and multiple layers of probe modules can be employed to achieve complete coverage of the test surface. The radial cross-sectional shapes of the test objects can be of round or polygonal. This design is suitable for inspection lines in production facilities and would not be suitable for assessing surface discontinuities and wear in off road vehicle rims and wheels.

Flexible probes that are strap-like have been disclosed. These can be pressed into round-edged shapes, for example, pipeline, tube inspection, and aircraft. However, they are only useful for assessing wear and integrity of smooth surfaces and are subject to wear if used on hard edges or rough surfaces.

A patent pending flexible probe array (FPA) configured in a glove that can be worn by an inspector has been disclosed. The FPA conforms to the inspection surface and allows inspection of a wide region with each scan of the array. With this arrangement, the operator receives tactile feedback of surface profile changes and is able to adjust the pressure on the FPA to accommodate changing geometries. The FPA approach eliminates the need to maintain probe alignment and the raster scanning needed with a conventional probe. The system has been successfully demonstrated at four operating power plants. A major deficiency is that it relies heavily on the proficiency of the user and therefore there is a risk of human error. Further, the results would vary from operator to operator as there is no accurate feedback to the operator to ensure consistency between operators. In addition, the scan coverage on the glove is very small. Still further, the flexible probe would be ill suited for environments where there is dust, dirt and potentially an abrasive test surface.

Current practices for inspecting off road vehicle wheels and rims, particularly in the mining sector, involves shipping wheels and rims to a central facility for inspection, repair and certification. This facility may be hundreds of miles from the mine site. When at the facility, electromagnetic, in particular, Magnetic Particle Inspection is conducted. Approximately 50% of the wheels and rims shipped from a mine site to a central facility are in good condition. The logistics of this is cumbersome but is the only option available to mining customers. Further to this, the assessment is a visual assessment, therefore depending on the skill and experience of the assessor. Still further, the data are not electronically acquired and stored and must, therefore, be manually entered should an archive be desired.

The most critical region for examination on an OTR wheel and rim is where metal meets metal. The sections which have direct contact with the truck and assembly parts are the gutter section, back section, mounting disc (knave) and or mounting taper (rim). The gutter section of an OTR rim or wheel base has 4 distinct individual groove patterns (HDT, EM, EMH, & EV). The groove design is usually selected based on rim size and application. The back section has 3 distinct manufacture designs (Standard/MES, TSR & IGLR/Wedge). Selection of the back section design is related to tire support and positioning on the truck. Significantly, there are seven main rim profiles used in OTR mining truck vehicles. There are also various wheel and rim profiles for graders, loaders, logging trucks and other off road vehicles.

What is needed therefore is a probe and method suited to field testing to accurately and quickly identify defects and wear. The method would preferably not rely on visual inspection. It would be preferable if the probe allowed for a quantitative measure of wear and it there was a standard and method for assessing pass/fail using such probe. It would be further preferably if only defects of significance to the certification of the wheels and rims of off road vehicles were identified. It would be of further advantage if wear on the probe could be reduced, and if probe life could be extended. It would be advantageous if the resulting data were sent directly to a computer, analyzed, displayed in three dimensions and archived. It would be of a still greater advantage if the data could be used to develop predictive models for subsequent scheduling of testing.

SUMMARY

The present technology is directed to probes and a method for testing rolled steel wheels and rolled steel rims in the field for defects and wear. As abrasion is a significant concern when testing rough surfaces, a resilient surface has been provided to reduce wear. This is a replaceable layer, thus increasing the life of the probe and reducing down time. The method is quick and accurate, resulting in little downtime. The method provides a quantitative measure of wear with little opportunity for human error. The eddy current array configuration is designed specifically for detecting significant defects that would result in the rim being taken out of commission. Both rigid and conformable probes have been developed. As the data are acquired electronically, the results can be analyzed, displayed in three dimensions and archived by the receiving computer. By including a time stamp with the data, predictive models can be developed to schedule subsequent testing, based on hours of use.

In one embodiment a method of examining a wheel or rim on site is provided. The method uses a system comprising an eddy current array probe in electronic communication with a computer, the eddy current array probe including a resilient surface overtop a sensor layer, the computer having a processor and a memory, the memory to provide instructions to the processor. The method comprises: standardizing the eddy current array probe with a reference standard; adjusting the eddy current array probe with a lift off screw to provide a suitable distance between the probe and a surface of the wheel or rim; scanning the wheel or rim with an alternating current; sending a data set to the computer; the computer analyzing the data set; and the computer displaying a three-dimensional image of the data set on a user interface.

The method may further comprise the computer archiving the data set.

In the method, the wheel or rim may be examined for a surface discontinuity.

In the method, the wheel or rim may be examined for a sub-surface discontinuity.

In the method, the wheel or rim may be examined for both a surface and a sub-surface discontinuity.

In the method, the wheel or rim may be from an off road vehicle.

In the method, on site may be a mine site.

The method further comprises multiplexing the data set.

In another embodiment a system for assessing integrity of a wheel or a rim of a mining vehicle on site is provided, the system comprising: an eddy current array probe, the eddy current array probe including a series of drive coils and a series of sensing coils, a multiplexer, and a plurality of data channels; a computer, the computer including a processor and a memory, the memory to provide instructions to the processor; and a user interface.

In the system, the series of sensing coils may be arranged in an at least two rows, the at least two rows offset by a half of a coil.

In another embodiment, a method of assessing integrity of a wheel or rim of a mining vehicle on site is provided, the method comprising using the system described above.

In the method, the wheel or rim may be examined for a surface discontinuity.

In the method, the wheel or rim may be examined for a sub-surface discontinuity.

In the method, the wheel or rim may be examined for both a surface and a sub-surface discontinuity.

In the method, the wheel or rim may be from an off road vehicle.

In another embodiment, a method of modeling wear on a wheel of an off road vehicle is provided, the method comprising i) selecting a wheel; ii) assessing wear by: setting a lift off screw to a predefined height; scanning the wheel with an eddy current array probe; reviewing the scan on an interface configured to communicate with a processor that is configured to communicate with the eddy current array probe and to analyze a scan; optionally adjusting the lift off screw to a second and subsequent predefined heights and scanning the wheel with the eddy current array probe, repeating until the scan indicates a lack of signal from the eddy current array to provide a datum; and time stamping the datum with hours of operation; iii) after a predefined numbers of hours of operation, repeating the assessment; and iv) preparing a predictive model based on wear over hours of operation.

In the method the lift off screw may be set at about 1.0 mm to about 2 mm.

In the method the eddy current array probe may comprise a resilient surface overtop a sensor layer.

In the method the resilient surface may be a film selected from the group consisting of Ultra-high-molecular-weight polyethylene (UHMW), High-density polyethylene (HDPE) or poly vinyl chloride.

In the method the resilient surface may be a removable UHMW adhesive-backed flexible plastic film.

In the method, the eddy current array probe may be a flexible probe.

In the method the flexible probe may comprise a conformable layer between a shoe and the sensor layer, the conformable layer having a Shore OO durometer rating of about OO15 to about OO60.

In another embodiment, an assembly for identifying a discontinuity in a wheel is provided, the assembly comprising an eddy current array probe, a user interface, at least one processor and at least one memory including computer programme controlling an output signal to the eddy current array probe and a computer programme to analysis an input signal, wherein the eddy current array probe comprises a resilient surface overtop a sensor layer.

In the assembly the resilient surface may be a film selected from the group consisting of Ultra-high-molecular-weight polyethylene (UHMW), High-density polyethylene (HDPE) and poly vinyl chloride.

In the assembly the resilient surface may be a removable UHMW adhesive-backed flexible plastic film.

In the assembly the eddy current array probe may be a flexible probe.

In the assembly the flexible probe may comprise a conformable layer between a shoe and the sensor layer, the conformable layer having a Shore OO durometer rating of about OO15 to about OO60.

In yet another embodiment, a method of examining a rolled steel wheel or rim on site is provided using a system comprising an eddy current array probe in electronic communication with a computer, the eddy current array probe including a resilient surface overtop a sensor layer, the resilient surface comprising a film comprising Ultra-high-molecular-weight polyethylene (UHMW), High-density polyethylene (HDPE) and poly vinyl chloride, the computer having a processor and a memory, the memory to provide instructions to the processor, the method comprising: standardizing the eddy current array probe with a reference standard; adjusting the eddy current array probe with a lift off screw to provide a suitable distance between the probe and a surface of the wheel or rim; scanning the wheel or rim with an alternating current; sending a data set to the computer; the computer analyzing the data set; and the computer displaying a three-dimensional image of the data set on a user interface.

In the method the resilient surface may be a removable UHMW adhesive-backed flexible plastic film.

In the method the eddy current array probe may be a flexible probe.

In the method the flexible probe may comprise a conformable layer between a shoe and the sensor layer, the conformable layer having a Shore OO durometer rating of about OO15 to about OO60.

FIGURES

FIG. 6 is a block diagram of the method of the present technology.

FIG. 7 is a block diagram of another method of the present technology.

DESCRIPTION

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, The terms "comprising," "having," "including," and "containing" are to be construed as open ended terms (i.e., meaning "including, but not limited to,") unless otherwise noted.

To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Figure 1:
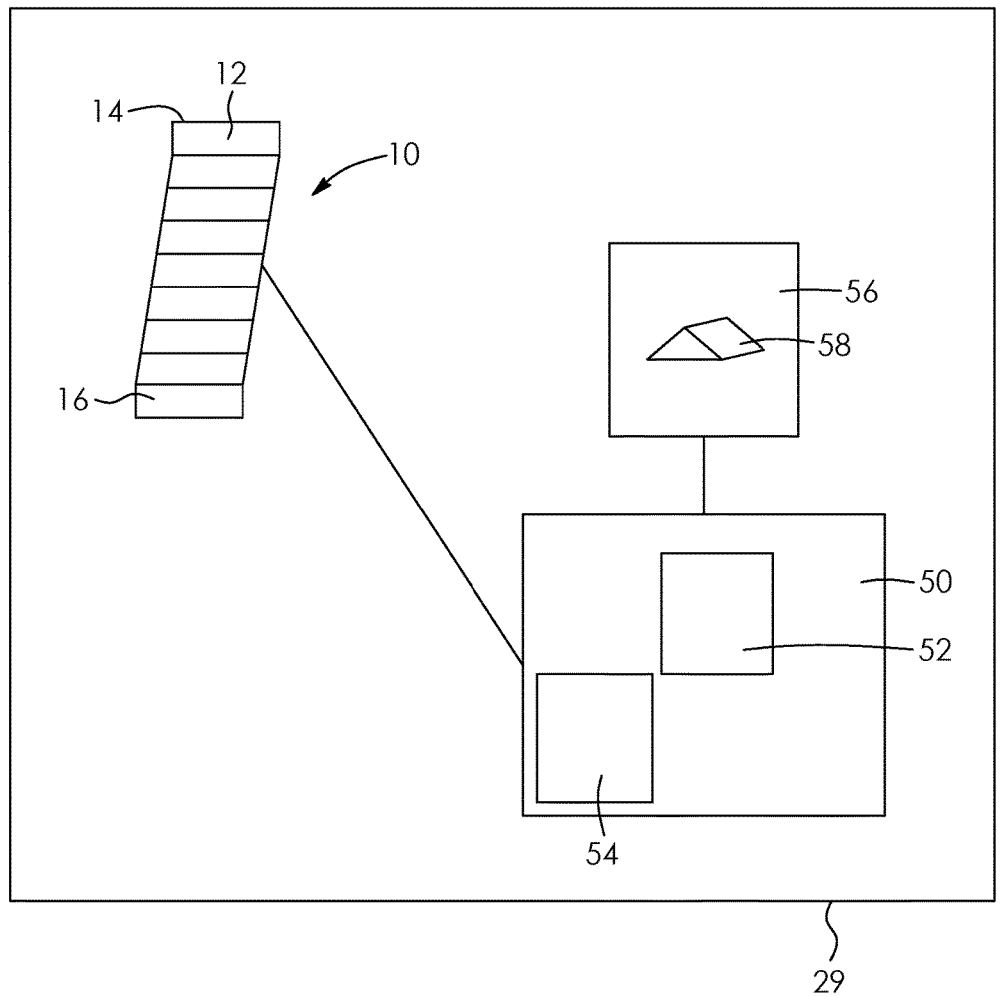
FIG. 1 is the system of the present technology.

As shown in FIG. 1, a generalized probe, generally referred to as 10, has a plurality of sensors 12 essentially covering the surface of the probe from a distal end 14 to a proximal end 16. The probe output is preferably a high frequency, ranging from about 50 kiloHertz (kHz) to about 700 kHz and all frequencies there between, for example, but not limited to about 500 kHz, as this is particularly well suited to detection of surface discontinuities. Both flexible and rigid probes that are shaped to conform to the shape of a wheel or a rim being assessed have been developed.

Three topologies were considered in the probe design:

a) Impedance Topology: absolute or differential, classic mode that offers high level of sensitivity, where minimal lift-off variation. This is capable of detecting discontinuities in any orientation.

b) Single-Drive Topology: transmit-receive mode where one coil acts as a transmitter and the other acts as a receiver. This is capable of detecting sub-surface discontinuities.

c) Double driver topology: acts in a transmit-receive mode, simultaneously uses two coils to act as a single large transmitter. This offers fine resolution and therefore has excellent detection capabilities.

As one objective of the present technology is to reduce, minimize or remove human error, the probe design specifically allows for measurement of surface cracks and does not penetrate further into the material being inspected. The design also specifically allows for detection of wear of about 2 mm, or about 3 mm or greater, and does not, when set to a pass/fail mode, detect wear of less than about 1 mm or about 2 mm, depending upon the setting. In the research and data collection mode, the lift off is set at set positions of about 0.25 mm, about 0.5 mm, about 0.75 mm and about 1.0 mm. This allows for data collection of wear over time at specific sites, allowing for predicting wear and scheduling testing. As testing requires that the wheel be taken off the truck and then the tire taken off the wheel, a predictive model can greatly reduce unnecessary labour and the associated down time for the vehicle.

Compilation of crack data collected from numerous tests show that cracks almost always start in a circumferential orientation, (x axis) then can branch off in an axial orientation (y axis). As it is the x axis crack that propagates the y axis crack, it was concluded that the probe design need only address x axis cracks, thus simplifying the probe design.

Returning to FIG. 1, the probe 10 is in communication with a computer 50, the computer 50 having a processor 52 to receive instructions from a memory 54. The computer 50 converts the impedance information into physical property values for the material under examination, including the lift-off at each point in a B-scan or a C-scan. The computer 50 may be integrated into the probe 10. The computer 50 is in electronic communication with a user interface 56, which can display three-dimensional images 58. The eddy current array probe 10 and computer 50 are used in the method of the present technology. The instrument 29 and computer 50 can be one complete unit.

Figure 2:
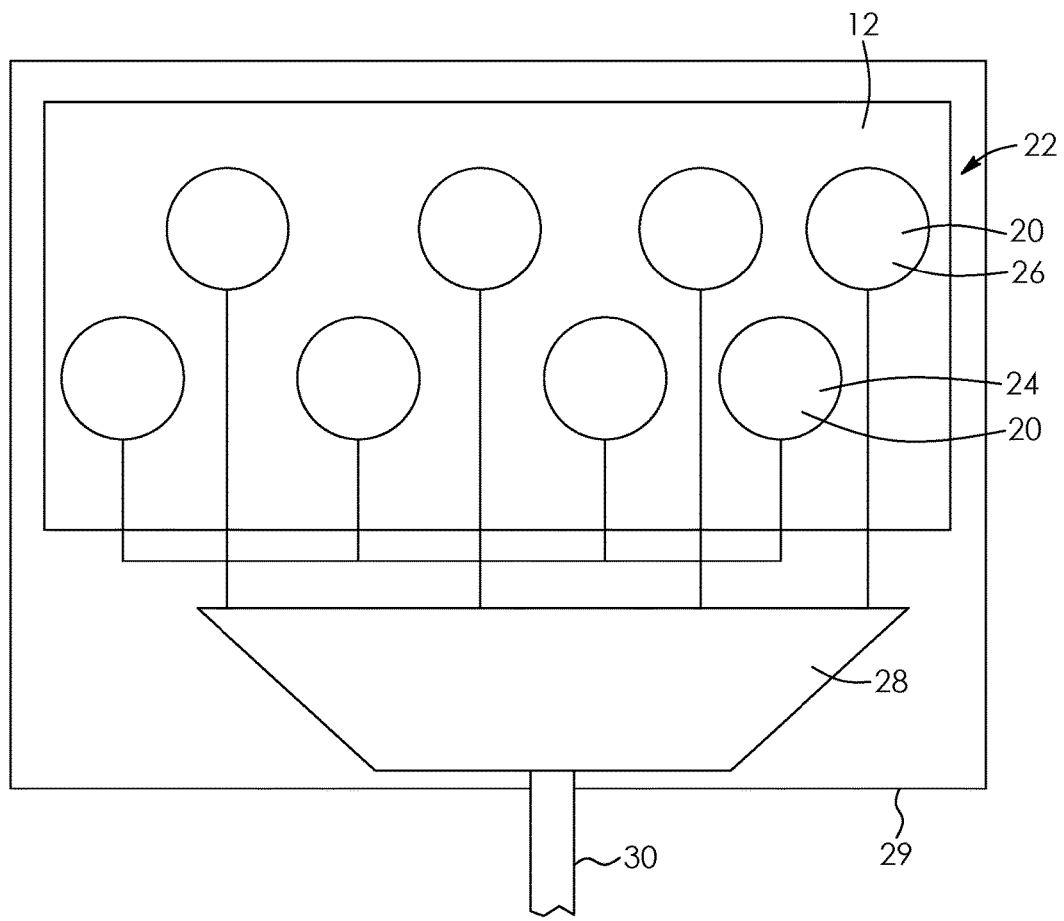
FIG. 2 shows the coil array of a probe of the system of FIG. 1.

As shown in FIG. 2, the sensors 12 have a plurality of pancake coils 20 to form an eddy current array, generally referred to as 22. There are at least two rows of coils 20 offset by half a coil 20. The array 22 is designed to cover the surface to be analyzed. There are drive coils 24 and sensing coils 26. The surface array has: (1) a linear drive conductor and one or more linear arrays of sensing coils positioned parallel to the drive conductor, where the second linear array is aligned with the first row to add redundancy or offset to improve image resolution in the direction transverse to the scan direction; (2) a complex drive conductor that produces a desired field pattern at each sensing coil; and (3) individual drive conductors associated with each sensing coil.

The signals from the eddy current array 22 may pass through a multiplexer 28 and then to data channels 30. The multiplexer 28 can be internal in the instrument 29 or external, separate from the instrument. It is used when the number of sensing coils 26 for impedance measurement is greater than the number of channels 30.

Figure 3:
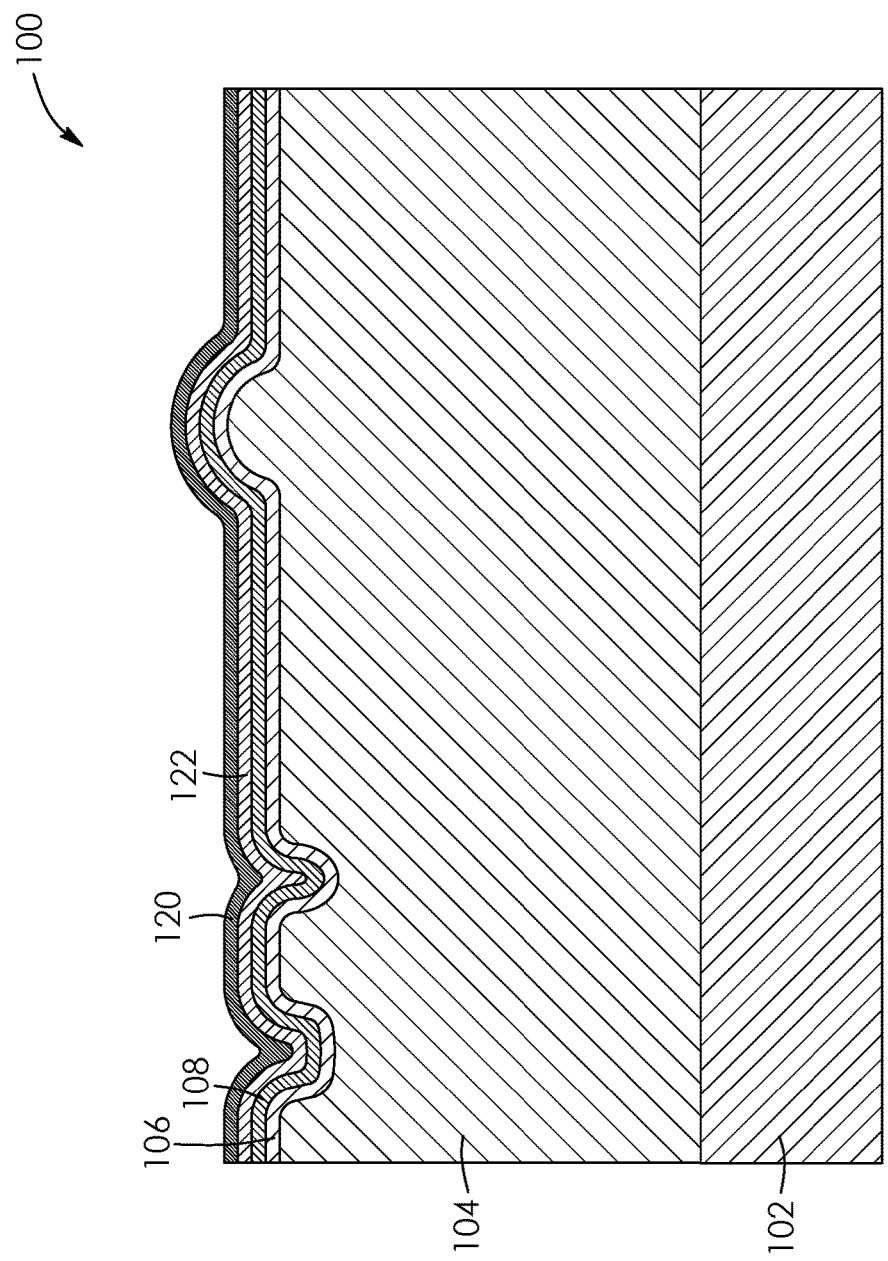
FIG. 3 is a flexible probe.

As shown in FIG. 3, a flexible probe, generally referred to as 100, has a holder 102, a shoe 104, a conformable layer 106, a sensor layer 108 and a resilient surface 120. The probe output is preferably a high frequency, ranging from about 50 kiloHertz (kHz) to about 500 kHz or about 700 kHz. The shoe 104 is shaped generally to conform to the shape of the article being tested, but is not specifically shaped to the exact shape. This allows one probe to be used for different wheel and rim sizes and shapes. The shoe 104 is preferably made of thermoplastic elastomers (TPE). The conformable layer 106 is, for example, but not limited to, foam. As determined through experimentation, the preferred Shore OO durometer rating of the conformable layer is about OO15 to about OO60, preferably about OO20 to about OO50 and most preferably OO25 and all ranges therein. This layer is pliable and formable, so it can conform to the shape of the article being assessed. The resilient surface 120 is flexible and can be bent to the shape of the article being assessed. It is long wearing and resistant to scratching. The resilient surface 120 is preferably a plastic polymeric material, such as, but not limited to Ultra-high-molecular-weight polyethylene (UHMW), High-density polyethylene (HDPE), poly vinyl chloride or similar, slippery plastic. A preferred surface is a removable UHMW adhesive-backed flexible plastic film. It has a low coefficient of friction and a high abrasion resistance. If a non-adhesive resilient surface is employed, then it is glued to the sensor layer 108 with a releasable adhesive layer 122. This allows for replacement of the resilient surface 120, as needed.

Figure 4:
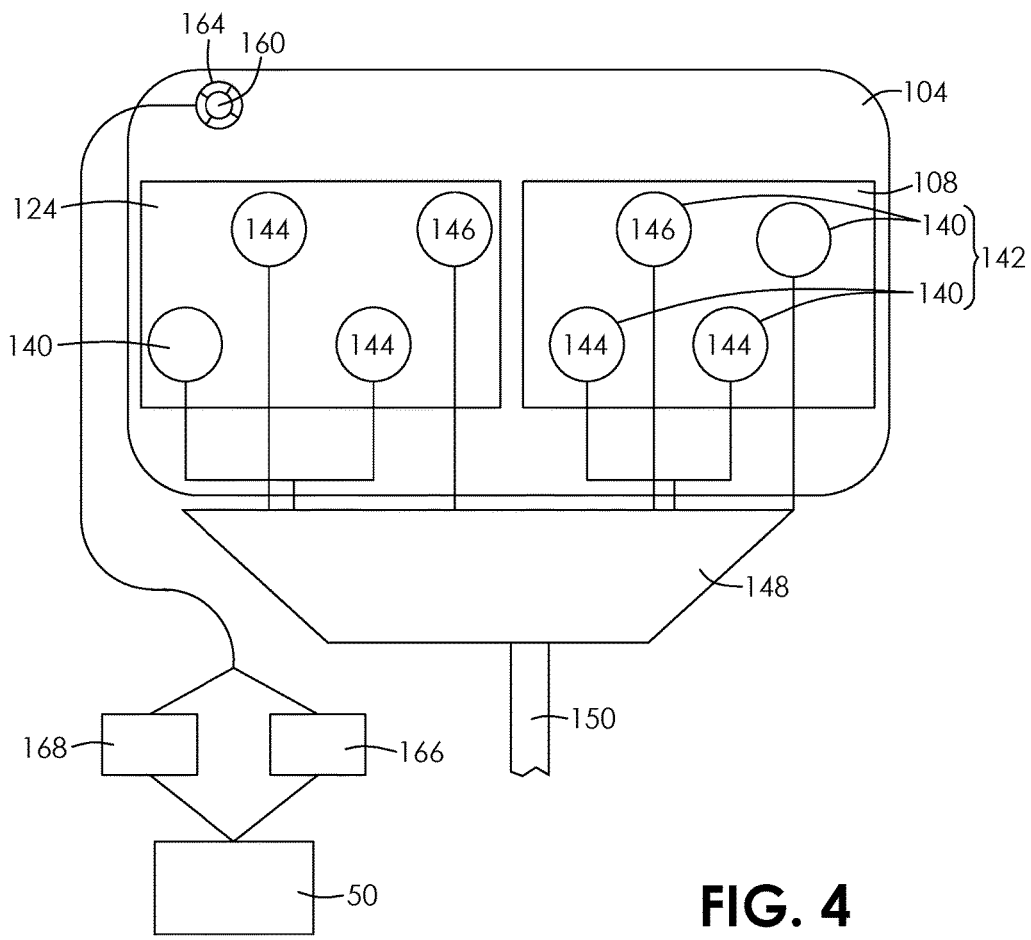
FIG. 4 shows the coil array of the flexible probe.

As shown in FIG. 4, the sensor layer 108 is comprised of a plurality of sensors 124. It is a flexible layer and is affixed to the shoe 104 with an adhesive. Each sensor 124 has a plurality of coils 140 to form an eddy current array, generally referred to as 142. There are drive coils 144 and sensing coils 146. The signals from the eddy current array 142 may pass through a multiplexer 148 and then to data channels 150. A lift off screw 160 is attached to the probe 100 and extends outward from the probe 100. It has factory settings that allow for only specific lift offs to be used. For pass/fail testing, the lift off is 2 mm. A gauge 164 on the lift off screw 160 is in electronic communication with the computer 50, either directly or through a processor 166 or circuit board 168. This ensures that the lift off is recorded with the test results, again mitigating the risk of user error. This is especially important when the lift off can be adjusted for pass/fail testing or can be used to collect wear data over time, for predictive purposes.

Figure 5:
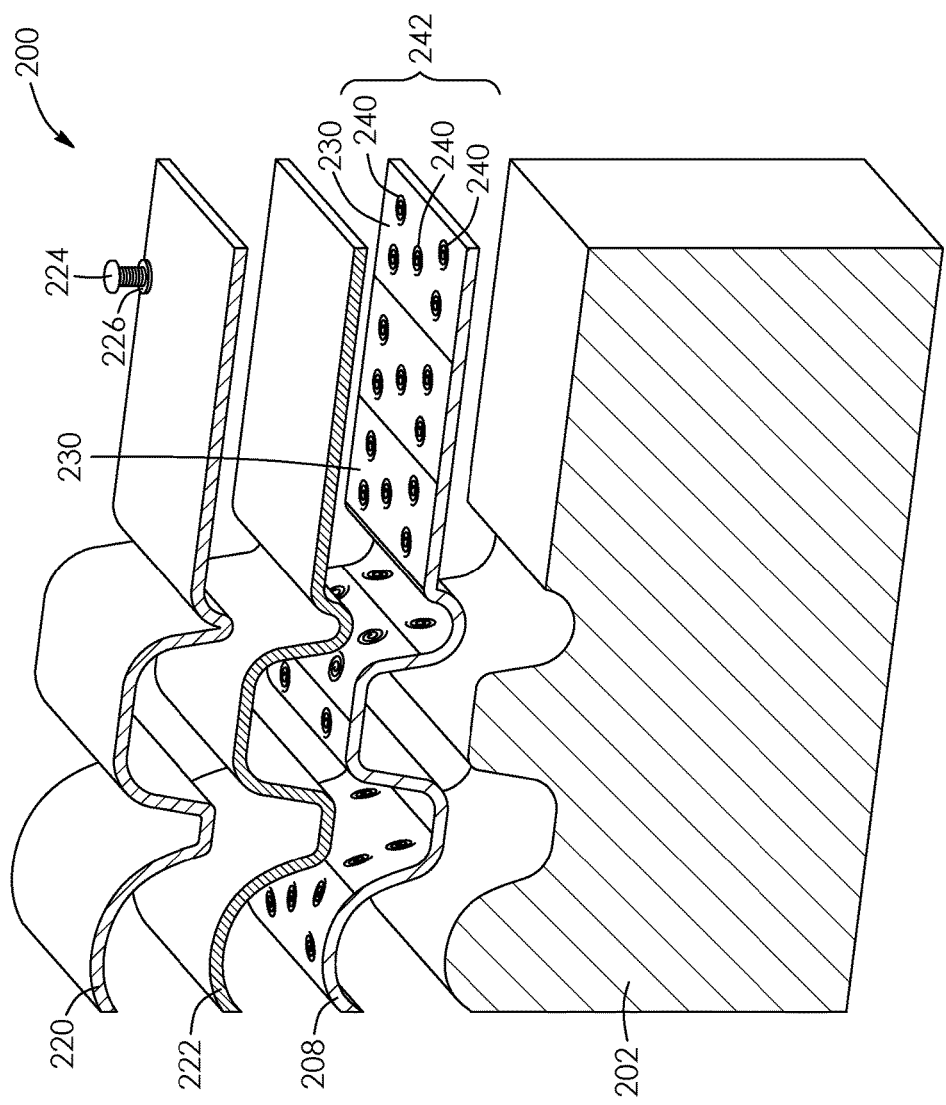
FIG. 5 is an exemplary rigid probe of the present technology.

An exemplary rigid probe design, generally referred to as 200 is shown in FIG. 5. The rigid probe 200 has a holder 202, a sensor layer 208 and a resilient surface 220. The probe output is preferably a high frequency, ranging from about 50 kiloHertz (kHz) to about 500 kHz or about 700 kHz. The sensor layer 208 has a plurality of sensors 230. Each sensor 230 has a plurality of coils 240 to form an eddy current array, generally referred to as 242. The probe 200 is shaped specifically to conform to the shape of the article being tested. The resilient surface 220 is flexible and is bent to the shape of the probe 200. It is long wearing and resistant to scratching. The resilient surface 220 is preferably a plastic polymeric material, such as, but not limited to Ultra-high-molecular-weight polyethylene (UHMW), High-density polyethylene (HDPE), poly vinyl chloride or similar, slippery plastic. A preferred surface is a removable UHMW adhesive-backed flexible plastic film. It has a low coefficient of friction and a high abrasion resistance. If a non-adhesive resilient surface is employed, then it is glued to the sensor layer 208 with a releasable adhesive layer 222. This allows for replacement of the resilient surface 220, as needed. A lift off screw 224 is attached to the probe 200 and extends outward from the probe 200. It has factory settings that allow for only specific lift offs to be used. For pass/fail testing, the lift off is 2 mm. A gauge 226 on the lift off screw 224 is in electronic communication with the computer 50, either directly or through a processor 228 or circuit board 230, as shown in FIG. 4.

An overview of the method is shown in FIG. 6. The method is used for crack detection, wear patterns and early signs of pitting in off road vehicle wheels and rim, on site. The part to be assessed is cleaned 400. There is no need to remove paint or any surface coating. A reference standard is used to standardize 402 all the channels of the array. The probe is placed 404 on the surface of the part to be assessed, and the lift off is set 408 the surface is scanned 410 with an alternating current. The scan speed is controlled 412. If there are no defects the alternating current produces 414 a uniform magnetic field above the surface. If there are defects, the alternating current leads 416 to a non-uniform magnetic field. The signal provides 418 position and depth information. This signal is then processed 420 by the processor using instructions provided 422 by the memory to provide 424 depth, length and position information with regard to cracks. Data can be analyzed from individual coil channels or for the entire surface. A three dimensional image is produced 426 and displayed 428 on the user interface. The data are archived 430 in the memory for future reference. The probe will detect surface discontinuities and wear can be determined from the lift off data provided, thereby providing a complete assessment of the integrity of the wheel or rim.

As shown in FIG. 7, if wear is to be determined lift off is set 408 at 2 mm for pass/fail assessment or at one of 0.5, 1.0, or 1.5 mm for data collection. This can be done separately, or in conjunction with examining for surface discontinuities. If there is wear that is greater than the lift off setting, the probe will fail to send a signal 452. The processor uses 454 instructions from the memory. The lack of signal or presence of signal is then processed 456 by the processor to provide a pass reading 458 or a fail reading 460. If used for data collection, the memory will provide 462 instructions to the processor and the processor will process 464 the lack of signal to provide 466 data on wear, shape of wear area and position information. This can be further processed 468 using date stamps to produce 470 predictive models for wear.

Through experimentation, it has been determine that rims and wheels that have lost 2 mm or more metal should be taken out of service. This can be from wear or pitting. By setting lift off to 2 mm, if the area being inspected has lost 2 mm or more metal, the eddy current array doesn't detect the worn area, there is no signal, the display indicates lift-off and the rim is therefore removed from service. This therefore is a quantitative assessment that minimizes any human error.

If desired, a magnetic particle examination occurs. This is not essential as it does not provide any additional information.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific example embodiments specifically described herein. For example, other imaging techniques may be used, resulting in other images being analyzed. Such equivalents are intended to be encompassed in the scope of the claims, if appended hereto or subsequently filed.

The invention claimed is:

1. A method of examining a steel wheel or steel rim on site, the method comprising: selecting a system including an eddy current array probe in electronic communication with a computer, the eddy current array probe including a replaceable, resilient exterior surface overtop a sensor layer, the computer having a processor and a memory, the memory to provide instructions to the processor, the method comprising: standardizing the eddy current array probe with a reference standard; adjusting the eddy current array probe to provide a lift off; scanning the wheel or rim with an alternating current; sending a data set to the computer; the computer analyzing the data set; and the computer displaying a three-dimensional image of the data set on a user interface.

2. The method of claim 1 further comprising the computer archiving the data set.

3. The method of claim 2, wherein the eddy current array probe is a flexible probe.

4. The method of 3, wherein the lift off is set at 2 mm to 3 mm, to provide a quantitative measurement or at one of 0.5, 1.0, or 1.5 mm for data collection.

5. The method of claim 4, further comprising passing or failing the wheel or rim based on the quantitative measurement.

6. The method of claim 5, wherein the wheel or rim is inspected for one or more of a surface discontinuity and wear.

7. The method of claim 4, wherein the replaceable, resilient exterior surface is a film selected from the group consisting of Ultra-high-molecular-weight polyethylene (UHMW), High-density polyethylene (HDPE) and poly vinyl chloride.

8. The method of claim 7, wherein the replaceable, resilient exterior surface is a removable UHMW adhesive-backed flexible plastic film.

9. The method of claim 8, wherein on site is a mine site.

* * * * *